(12) United States Patent
Deckman et al.

(10) Patent No.: US 12,048,583 B2
(45) Date of Patent: *Jul. 30, 2024

(54) ABLATION DEVICE WITH ARTICULATED IMAGING TRANSDUCER

(71) Applicant: Gynesonics, Inc., Redwood City, CA (US)

(72) Inventors: Robert K. Deckman, San Bruno, CA (US); Brian Placek, Manhattan, KS (US); Michael A. Munrow, Belmont, CA (US); Craig Gerbi, Mountain View, CA (US); Jessica Grossman, Covington, KY (US)

(73) Assignee: Gynesonics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/782,477

(22) Filed: Feb. 5, 2020

(65) Prior Publication Data

US 2021/0015450 A1 Jan. 21, 2021

Related U.S. Application Data

(63) Continuation of application No. 14/989,732, filed on Jan. 6, 2016, now Pat. No. 10,610,197, which is a (Continued)

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/0841* (2013.01); *A61B 8/445* (2013.01); *A61B 8/4461* (2013.01);
(Continued)

(58) Field of Classification Search
CPC .................. A61B 8/12; A61B 18/1485; A61B 2017/00053; A61B 2017/3413;
(Continued)

(56) References Cited

U.S. PATENT DOCUMENTS 4,289,132 A 9/1981 Rieman
4,802,487 A 2/1989 Martin et al.
(Continued)

FOREIGN PATENT DOCUMENTS

WO WO-9717105 A1 5/1997
WO WO-9811834 A1 3/1998
(Continued)

OTHER PUBLICATIONS

Alterovitz, et al. Simulating Needle Insertion and Radioactive Seed Implantation for Prostate Brachytherapy. Medicine Meets Virtual Reality 11, Westwood et al. (Eds.), IOS Press, Jan. 2003, pp. 19-25.
(Continued)

*Primary Examiner* — Michael T Rozanski
(74) *Attorney, Agent, or Firm* — Wilson Sonsini Goodrich & Rosati

(57) ABSTRACT

A system for imaging and treating tissue comprises a probe having a deflectable distal tip for carrying an imaging array and a delivery needle for advancement within a field of view of the imaging array. Optionally, the needle will carry a plurality of tines which may be selectively radially deployed from the needle. The imaging array will preferably be provided in a separate, removable component.

3 Claims, 12 Drawing Sheets

Related U.S. Application Data continuation of application No. 13/484,076, filed on May 30, 2012, now Pat. No. 10,595,819, which is a continuation-in-part of application No. 13/023,383, filed on Feb. 8, 2011, now Pat. No. 8,206,300, and a continuation-in-part of application No. 12/973,587, filed on Dec. 20, 2010, now Pat. No. 8,506,485, said application No. 13/023,383 is a continuation of application No. PCT/US2009/054956, filed on Aug. 25, 2009, which is a continuation-in-part of application No. 12/198,861, filed on Aug. 26, 2008, now abandoned, said application No. 12/973,587 is a continuation of application No. 11/564,164, filed on Nov. 28, 2006, now Pat. No. 7,874,986, which is a continuation-in-part of application No. 11/409,496, filed on Apr. 20, 2006, now Pat. No. 7,815,571.

(51) Int. Cl.
    *A61B 8/08* (2006.01)
    *A61B 18/14* (2006.01)
    *A61B 17/34* (2006.01)
    *A61B 18/00* (2006.01)
    *A61B 90/00* (2016.01)

(52) U.S. Cl.
    CPC .. *A61B 18/1485* (2013.01); *A61B 2017/3413* (2013.01); *A61B 2018/0016* (2013.01); *A61B 2018/00559* (2013.01); *A61B 2018/00577* (2013.01); *A61B 2018/1425* (2013.01); *A61B 2018/143* (2013.01); *A61B 2018/1432* (2013.01); *A61B 2018/1475* (2013.01); *A61B 2090/3782* (2016.02); *A61B 2090/3784* (2016.02)

(58) Field of Classification Search
    CPC .... A61B 2017/4216; A61B 2018/0016; A61B 2018/00559; A61B 2018/00577; A61B 2018/1425; A61B 2018/143; A61B 2018/1432; A61B 2018/1475; A61B 2034/107; A61B 2034/256; A61B 2090/378; A61B 2090/3782; A61B 2090/3784; A61B 2090/3975; A61B 34/10; A61B 34/20; A61B 34/25; A61B 5/4325; A61B 8/08; A61B 8/0841; A61B 8/445; A61B 8/4461; A61B 90/37; G06F 3/0484; G16H 40/63
    See application file for complete search history.

(56) References Cited

U.S. PATENT DOCUMENTS

| | | | |
|---|---|---|---|
| 4,936,281 A | 6/1990 | Stasz |
| 5,372,587 A | 12/1994 | Hammerslag et al. |
| 5,456,689 A | 10/1995 | Kresch et al. |
| 5,469,853 A | 11/1995 | Law et al. |
| 5,471,988 A | 12/1995 | Fujio et al. |
| 5,492,126 A | 2/1996 | Hennige et al. |
| 5,527,331 A | 6/1996 | Kresch et al. |
| 5,531,676 A | 7/1996 | Edwards et al. |
| 5,607,389 A | 3/1997 | Edwards et al. |
| 5,649,911 A | 7/1997 | Trerotola |
| 5,662,664 A | 9/1997 | Gordon et al. |
| 5,666,954 A | 9/1997 | Chapelon et al. |
| 5,697,897 A | 12/1997 | Buchholtz et al. |
| 5,730,752 A | 3/1998 | Alden et al. |
| 5,741,287 A | 4/1998 | Alden et al. |
| 5,769,880 A | 6/1998 | Truckai et al. |
| 5,800,378 A | 9/1998 | Edwards et al. |
| 5,860,974 A | 1/1999 | Abele et al. |
| 5,863,294 A | 1/1999 | Alden |
| 5,873,828 A | 2/1999 | Fujio et al. |
| 5,876,340 A | 3/1999 | Tu et al. |
| 5,876,399 A | 3/1999 | Chia et al. |
| 5,891,137 A | 4/1999 | Chia et al. |
| 5,906,615 A | 5/1999 | Thompson |
| 5,908,385 A | 6/1999 | Chechelski et al. |
| 5,916,198 A | 6/1999 | Dillow |
| 5,931,787 A | 8/1999 | Dietz et al. |
| 5,957,941 A | 9/1999 | Ream |
| 5,964,740 A | 10/1999 | Ouchi |
| 5,979,452 A | 11/1999 | Fogarty et al. |
| 5,979,453 A | 11/1999 | Savage et al. |
| 5,984,942 A | 11/1999 | Alden et al. |
| 6,002,968 A | 12/1999 | Edwards |
| 6,007,499 A | 12/1999 | Martin et al. |
| 6,032,673 A | 3/2000 | Savage et al. |
| 6,039,748 A | 3/2000 | Savage et al. |
| 6,055,449 A | 4/2000 | Navab |
| 6,059,766 A | 5/2000 | Greff |
| 6,077,257 A | 6/2000 | Edwards et al. |
| 6,080,150 A | 6/2000 | Gough |
| 6,141,577 A | 10/2000 | Rolland et al. |
| 6,146,378 A | 11/2000 | Mikus et al. |
| 6,146,380 A | 11/2000 | Racz et al. |
| 6,158,250 A | 12/2000 | Tibbals, Jr. et al. |
| 6,171,249 B1 | 1/2001 | Chin et al. |
| 6,190,383 B1 | 2/2001 | Schmaltz et al. |
| 6,193,714 B1 | 2/2001 | Mcgaffigan et al. |
| 6,211,153 B1 | 4/2001 | Garnick et al. |
| 6,216,029 B1 | 4/2001 | Paltieli |
| 6,238,336 B1 | 5/2001 | Ouchi |
| 6,254,601 B1 | 7/2001 | Burbank et al. |
| 6,280,441 B1 | 8/2001 | Ryan |
| 6,296,639 B1 | 10/2001 | Truckai et al. |
| 6,306,129 B1 | 10/2001 | Little et al. |
| 6,315,741 B1 | 11/2001 | Martin et al. |
| 6,355,275 B1 | 3/2002 | Klein |
| 6,379,348 B1 | 4/2002 | Onik |
| 6,405,732 B1 | 6/2002 | Edwards et al. |
| 6,419,648 B1 | 7/2002 | Vitek et al. |
| 6,419,653 B2 | 7/2002 | Edwards et al. |
| 6,419,673 B1 | 7/2002 | Edwards et al. |
| 6,425,867 B1 | 7/2002 | Vaezy et al. |
| 6,432,067 B1 | 8/2002 | Martin et al. |
| 6,447,477 B2 | 9/2002 | Burney et al. |
| 6,461,296 B1 | 10/2002 | Desai |
| 6,463,331 B1 | 10/2002 | Edwards |
| 6,482,203 B2 | 11/2002 | Paddock et al. |
| 6,485,413 B1 | 11/2002 | Boppart et al. |
| 6,506,154 B1 | 1/2003 | Ezion et al. |
| 6,506,156 B1 | 1/2003 | Jones et al. |
| 6,506,171 B1 | 1/2003 | Vitek et al. |
| 6,507,747 B1 | 1/2003 | Gowda et al. |
| 6,508,815 B1 | 1/2003 | Strul et al. |
| 6,522,142 B1 | 2/2003 | Freundlich |
| 6,540,677 B1 | 4/2003 | Angelsen et al. |
| 6,543,272 B1 | 4/2003 | Vitek |
| 6,550,482 B1 | 4/2003 | Burbank et al. |
| 6,554,780 B1 | 4/2003 | Sampson et al. |
| 6,559,644 B2 | 5/2003 | Froundlich et al. |
| 6,569,159 B1 | 5/2003 | Edwards et al. |
| 6,572,613 B1 | 6/2003 | Ellman et al. |
| 6,579,298 B1 | 6/2003 | Bruneau et al. |
| 6,589,237 B2 | 7/2003 | Woloszko et al. |
| 6,592,559 B1 | 7/2003 | Pakter et al. |
| 6,602,251 B2 | 8/2003 | Burbank et al. |
| 6,610,054 B1 | 8/2003 | Edwards et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,623,481 B1 | 9/2003 | Garbagnati et al. |
| 6,626,854 B2 | 9/2003 | Friedman et al. |
| 6,626,855 B1 | 9/2003 | Weng et al. |
| 6,632,193 B1 | 10/2003 | Davison et al. |
| 6,635,055 B1 | 10/2003 | Cronin |
| 6,635,065 B2 | 10/2003 | Burbank et al. |
| 6,638,275 B1 | 10/2003 | Mcgaffigan et al. |
| 6,638,286 B1 | 10/2003 | Burbank et al. |
| 6,645,162 B2 | 11/2003 | Friedman et al. |

(56) References Cited

U.S. PATENT DOCUMENTS

| | | | |
|---|---|---|---|
| 6,645,202 B1 | 11/2003 | Pless et al. |
| 6,652,516 B1 | 11/2003 | Gough |
| 6,660,002 B1 | 12/2003 | Edwards et al. |
| 6,660,024 B1 | 12/2003 | Flaherty et al. |
| 6,663,624 B2 | 12/2003 | Edwards et al. |
| 6,663,626 B2 | 12/2003 | Truckai et al. |
| 6,666,833 B1 | 12/2003 | Friedman et al. |
| 6,679,855 B2 | 1/2004 | Horn et al. |
| 6,685,639 B1 | 2/2004 | Wang et al. |
| 6,689,128 B2 | 2/2004 | Sliwa et al. |
| 6,692,490 B1 | 2/2004 | Edwards |
| 6,701,931 B2 | 3/2004 | Sliwa et al. |
| 6,705,994 B2 | 3/2004 | Vortman et al. |
| 6,712,815 B2 | 3/2004 | Sampson et al. |
| 6,716,184 B2 | 4/2004 | Vaezy et al. |
| 6,719,755 B2 | 4/2004 | Sliwa et al. |
| 6,728,571 B1 | 4/2004 | Barbato |
| 6,730,081 B1 | 5/2004 | Desai |
| 6,735,461 B2 | 5/2004 | Vitek et al. |
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,790,180 B2 | 9/2004 | Vitek |
| 6,805,128 B1 | 10/2004 | Pless et al. |
| 6,805,129 B1 | 10/2004 | Pless et al. |
| 6,813,520 B2 | 11/2004 | Truckai et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,921,398 B2 | 7/2005 | Carmel et al. |
| 6,936,048 B2 | 8/2005 | Hurst |
| 6,944,490 B1 | 9/2005 | Chow |
| 6,969,354 B1 | 11/2005 | Marian |
| 6,994,706 B2 | 2/2006 | Chornenky et al. |
| 7,160,296 B2 | 1/2007 | Pearson et al. |
| 7,229,401 B2 | 6/2007 | Kindlein |
| 7,306,595 B2 | 12/2007 | Ostrovsky et al. |
| 7,387,628 B1 | 6/2008 | Behl et al. |
| 7,517,346 B2 | 4/2009 | Sloan et al. |
| 7,815,571 B2 | 10/2010 | Deckman et al. |
| 7,874,986 B2 | 1/2011 | Deckman et al. |
| 7,963,941 B2 | 6/2011 | Wilk |
| 8,080,009 B2 | 12/2011 | Lee et al. |
| 8,157,741 B2 | 4/2012 | Hirota |
| 8,157,745 B2 | 4/2012 | Schoot |
| 8,206,300 B2 * | 6/2012 | Deckman ............ A61B 8/0833 600/459 |
| 8,216,231 B2 | 7/2012 | Behl et al. |
| 8,221,321 B2 | 7/2012 | Mcmorrow et al. |
| 8,287,485 B2 | 10/2012 | Kimura et al. |
| 8,377,041 B2 | 2/2013 | Frassica et al. |
| 8,469,893 B2 | 6/2013 | Chiang et al. |
| 8,506,485 B2 | 8/2013 | Deckman et al. |
| 8,512,330 B2 | 8/2013 | Epstein et al. |
| 8,512,333 B2 | 8/2013 | Epstein et al. |
| 8,540,634 B2 | 9/2013 | Bruce et al. |
| 8,585,598 B2 | 11/2013 | Razzaque et al. |
| 8,622,911 B2 | 1/2014 | Hossack et al. |
| 8,663,130 B2 | 3/2014 | Neubach et al. |
| 8,718,339 B2 | 5/2014 | Tonomura et al. |
| 8,814,796 B2 | 8/2014 | Martin et al. |
| 8,992,427 B2 | 3/2015 | Munrow et al. |
| 9,089,287 B2 | 7/2015 | Sliwa et al. |
| 9,198,707 B2 | 12/2015 | Mckay et al. |
| 9,198,719 B2 | 12/2015 | Murdeshwar et al. |
| 9,247,925 B2 | 2/2016 | Havel et al. |
| 9,357,977 B2 | 6/2016 | Grossman |
| 9,439,627 B2 | 9/2016 | Case et al. |
| 9,510,898 B2 | 12/2016 | Epstein et al. |
| 9,516,996 B2 | 12/2016 | Diolaiti et al. |
| 10,595,819 B2 * | 3/2020 | Deckman ............ A61B 8/4461 |
| 10,610,197 B2 | 4/2020 | Deckman et al. |
| 2001/0014805 A1 | 8/2001 | Burbank et al. |
| 2001/0051802 A1 | 12/2001 | Woloszko et al. |
| 2002/0002393 A1 | 1/2002 | Mitchell |
| 2002/0022835 A1 | 2/2002 | Lee |
| 2002/0052600 A1 | 5/2002 | Davison et al. |
| 2002/0068871 A1 | 6/2002 | Mendlein et al. |
| 2002/0077550 A1 | 6/2002 | Rabiner et al. |
| 2002/0183735 A1 | 12/2002 | Edwards et al. |
| 2003/0009164 A1 | 1/2003 | Woloszko et al. |
| 2003/0014046 A1 | 1/2003 | Edwards et al. |
| 2003/0028111 A1 | 2/2003 | Vaezy et al. |
| 2003/0032896 A1 | 2/2003 | Bosley et al. |
| 2003/0130575 A1 | 7/2003 | Desai |
| 2003/0130655 A1 | 7/2003 | Woloszko et al. |
| 2003/0195420 A1 | 10/2003 | Mendlein et al. |
| 2003/0195496 A1 | 10/2003 | Maguire et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0006336 A1 | 1/2004 | Swanson |
| 2004/0030268 A1 | 2/2004 | Weng et al. |
| 2004/0054366 A1 | 3/2004 | Davison et al. |
| 2004/0120668 A1 | 6/2004 | Loeb |
| 2004/0143252 A1 | 7/2004 | Hurst |
| 2004/0153057 A1 | 8/2004 | Davison |
| 2004/0175399 A1 | 9/2004 | Schiffman et al. |
| 2004/0176760 A1 | 9/2004 | Qiu |
| 2004/0193028 A1 | 9/2004 | Jones et al. |
| 2004/0215182 A1 | 10/2004 | Lee |
| 2004/0230190 A1 | 11/2004 | Dahla et al. |
| 2004/0231772 A1 | 11/2004 | Leonard et al. |
| 2004/0254572 A1 | 12/2004 | Mcintyre et al. |
| 2005/0038340 A1 | 2/2005 | Vaezy et al. |
| 2005/0085730 A1 | 4/2005 | Flesch et al. |
| 2005/0107781 A1 | 5/2005 | Ostrovsky et al. |
| 2005/0124882 A1 | 6/2005 | Ladabaum et al. |
| 2005/0149013 A1 | 7/2005 | Lee |
| 2005/0177209 A1 | 8/2005 | Leung et al. |
| 2005/0197577 A1 | 9/2005 | Makin et al. |
| 2005/0215990 A1 | 9/2005 | Govari |
| 2005/0216039 A1 | 9/2005 | Lederman |
| 2005/0228288 A1 | 10/2005 | Hurst |
| 2005/0255039 A1 | 11/2005 | Desai |
| 2005/0256405 A1 | 11/2005 | Makin et al. |
| 2006/0010207 A1 | 1/2006 | Akerman et al. |
| 2006/0058680 A1 | 3/2006 | Solomon |
| 2006/0178665 A1 | 8/2006 | Sloan et al. |
| 2006/0184049 A1 | 8/2006 | Tsujita |
| 2006/0189972 A1 | 8/2006 | Grossman |
| 2006/0241368 A1 | 10/2006 | Fichtinger et al. |
| 2007/0006215 A1 | 1/2007 | Epstein et al. |
| 2007/0016183 A1 | 1/2007 | Lee et al. |
| 2007/0083082 A1 | 4/2007 | Kiser et al. |
| 2007/0161905 A1 | 7/2007 | Munrow |
| 2007/0179380 A1 * | 8/2007 | Grossman ............ A61B 8/4488 600/463 |
| 2007/0203486 A1 | 8/2007 | Young |
| 2007/0249936 A1 | 10/2007 | Deckman et al. |
| 2007/0249939 A1 | 10/2007 | Gerbi et al. |
| 2008/0033493 A1 | 2/2008 | Deckman et al. |
| 2008/0228081 A1 | 9/2008 | Becker et al. |
| 2009/0043295 A1 | 2/2009 | Arnal et al. |
| 2010/0056926 A1 | 3/2010 | Deckman et al. |
| 2010/0262133 A1 | 10/2010 | Hoey et al. |
| 2011/0288412 A1 | 11/2011 | Deckman et al. |
| 2012/0165813 A1 | 6/2012 | Lee et al. |
| 2012/0209115 A1 | 8/2012 | Tonomura |
| 2012/0271277 A1 | 10/2012 | Fischell et al. |
| 2012/0277737 A1 | 11/2012 | Curley |
| 2013/0281863 A1 | 10/2013 | Chiang et al. |
| 2013/0317366 A1 | 11/2013 | Hirayama et al. |
| 2014/0073910 A1 | 3/2014 | Munrow et al. |
| 2014/0180273 A1 | 6/2014 | Nair |
| 2014/0276081 A1 | 9/2014 | Tegels |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2016/0151041 A1 | 6/2016 | Lee et al. |

(56) References Cited

U.S. PATENT DOCUMENTS

| | | |
|---|---|---|
| 2016/0278740 A1 | 9/2016 | Negrila et al. |
| 2016/0310042 A1 | 10/2016 | Kesten et al. |
| 2021/0228179 A1* | 7/2021 | Munrow .............. A61B 8/0841 |

FOREIGN PATENT DOCUMENTS

| | | |
|---|---|---|
| WO | WO-9814169 A1 | 4/1998 |
| WO | WO-9943366 A1 | 9/1999 |
| WO | WO-0000098 A1 | 1/2000 |
| WO | WO-0180723 A2 | 11/2001 |
| WO | WO-0195819 A1 | 12/2001 |
| WO | WO-0211639 A1 | 2/2002 |
| WO | WO-0180723 A3 | 4/2002 |
| WO | WO-03005882 A2 | 1/2003 |
| WO | WO-03065908 A1 | 8/2003 |
| WO | WO-03005882 A3 | 11/2003 |
| WO | WO-2004002293 A2 | 1/2004 |
| WO | WO-2004002550 A2 | 1/2004 |
| WO | WO-2004020011 A1 | 3/2004 |
| WO | WO-2004035110 A2 | 4/2004 |
| WO | WO-2004035110 A3 | 6/2004 |
| WO | WO-2004058328 A2 | 7/2004 |
| WO | WO-2004064658 A1 | 8/2004 |
| WO | WO-2004002550 A3 | 10/2004 |
| WO | WO-2004058328 A3 | 10/2004 |
| WO | WO-2004002293 A3 | 7/2005 |
| WO | WO-2007124265 A2 | 11/2007 |
| WO | WO-2009158012 A2 | 12/2009 |

OTHER PUBLICATIONS

Bergamini, et al. Laparoscopic Radiofrequency Thermal Ablation: A New Approach to Symptomatic Uterine Myomas. Am. J. Obstetrics and Gynecology (2005) 192: 768-73.

CNN.com Health Women. Experimental technique uses lasers to shrink uterine fibroids. Nov. 28, 2000.

European search report and search opinion dated Oct. 16, 2015 for EP Application No. 09812027.2.

Hindley, et al. MRI guidance of focused ultrasound therapy of uterine fibroids: Early results. American Journal of Roentgenology, 2004, 183(6): 1173-1719.

International Search Report and Written Opinion dated Apr. 6, 2017 for International PCT Patent Application No. PCT/US2017/014753.

International search report and written opinion dated Oct. 13, 2009 for PCT/US2009/054956.

"IPRP for WO2017132153 Jul. 31, 2018".

Kanaoka, et al. Microwave endometrial ablation at a frequency of 2.45 Ghz. A pilot study. J Reprod Med. Jun. 2001; 46(60): 559-63.

Law, et al. Magnetic resonance-guided percutaneous laser ablation of uterine fibroids. J Magn Reson Imaging, Oct. 2000; 12(4):565-70.

Liu, et al. Catheter-Based Intraluminal Sonography. J. Ultrasound Med., 2004, 23:145-160.

Mogami, et al. Usefulness of MR-guided percutaneous cryotherapy. Med. Imaging Technol. 2004, 22(3): 131-6. (English abstract).

MSNBC OnLine Articles, About US: Articles; "Intrauerine Fibroids Can Now Be Treated Nonsurgically" http://www.fibroids.com/news-blog/2004/08/intrauterine-fibroids-can-now-be-treated-nonsurgically/ Aug. 23, 2004.

Notice of allowance dated Feb. 29, 2012 for U.S. Appl. No. 13/023,383.

Office action dated Mar. 4, 2011 for U.S. Appl. No. 12/198,861.
Office action dated Apr. 1, 2015 for U.S. Appl. No. 13/484,076.
Office action dated Apr. 5, 2016 for U.S. Appl. No. 13/484,076.
Office action dated Apr. 23, 2014 for U.S. Appl. No. 13/484,076.
Office action dated May 6, 2011 for U.S. Appl. No. 12/198,861.
Office Action dated Jun. 9, 2016 for U.S. Appl. No. 13/484,076.
Office action dated Jun. 24, 2013 for U.S. Appl. No. 13/484,076.
Office action dated Aug. 7, 2014 for U.S. Appl. No. 13/484,076.
Office Action dated Oct. 11, 2016 for U.S. Appl. No. 13/484,076.
Office Action dated Oct. 11, 2016 for U.S. Appl. No. 14/989,732.
Office action dated Oct. 17, 2013 for U.S. Appl. No. 13/484,076.
Office action dated Nov. 25, 2014 for U.S. Appl. No. 13/484,076.

Okamura, et al. Force Modeling for Needle Insertion into Soft Tissue. IEEE Transactions on Biomedical Engineering, Oct. 2001, 10 (51): 1707-1716.

RSNA 2000 Explore News Release. Lasers Liquify Uterine Fibroid Tumors. 11:30 a.m. CST, Monday, Nov. 27, 2000.

Senoh, et al. Saline Infusion Contrast Intrauterine Sonographic Assessment of the Endometrium with High-Frequency, Real-Time Miniature Transducer Normal Menstrual Cycle: a Preliminary Report. Human Reproduction, 14 (10): 2600-2603, 1999.

Vascular and Interventional Radiology, SRSC; Nonsurgical Treatment of Uterine Fibroids. Available at http://www.drfibroid.com/treatment.htm. Accessed Apr. 11, 2011.

Websand, Inc., New treatment options for fibroid tumors, Copyright 2002 by WebSand, Inc.

* cited by examiner

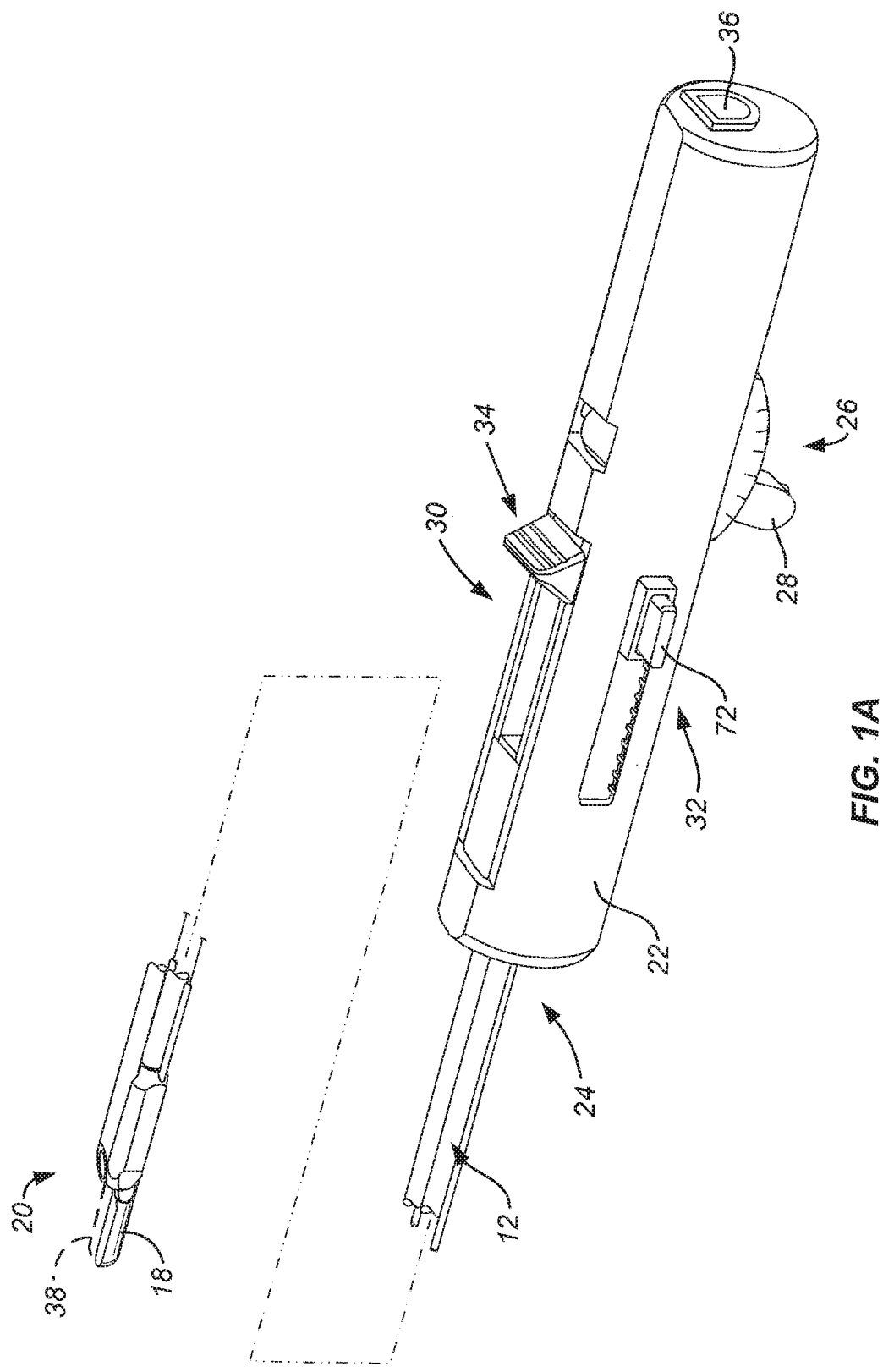

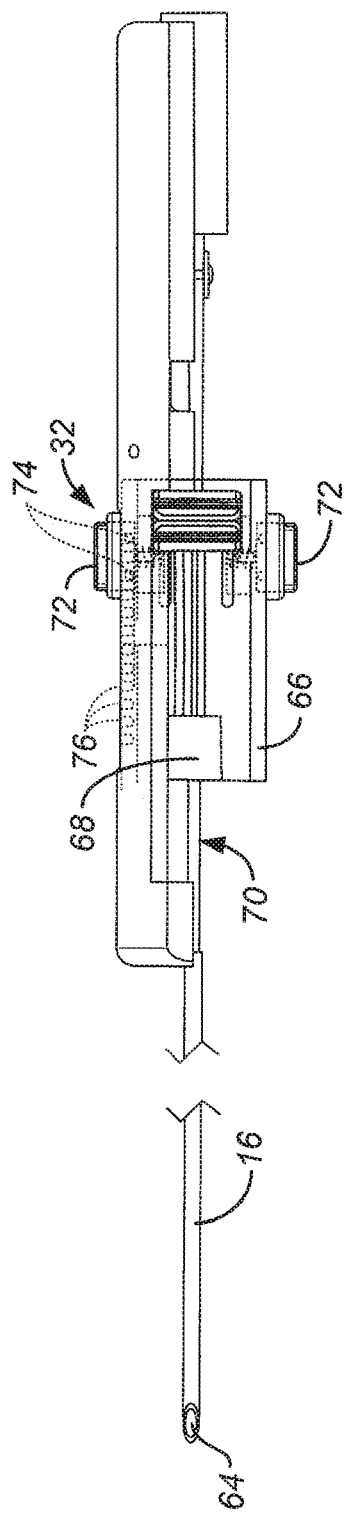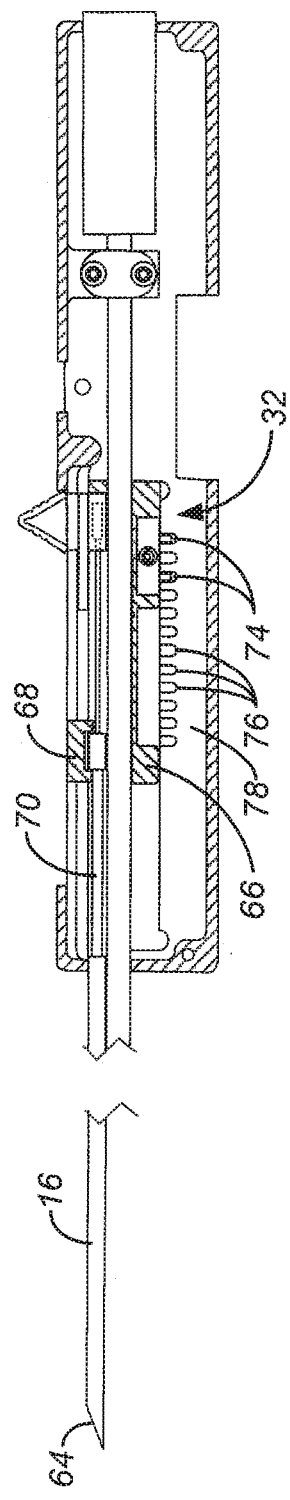

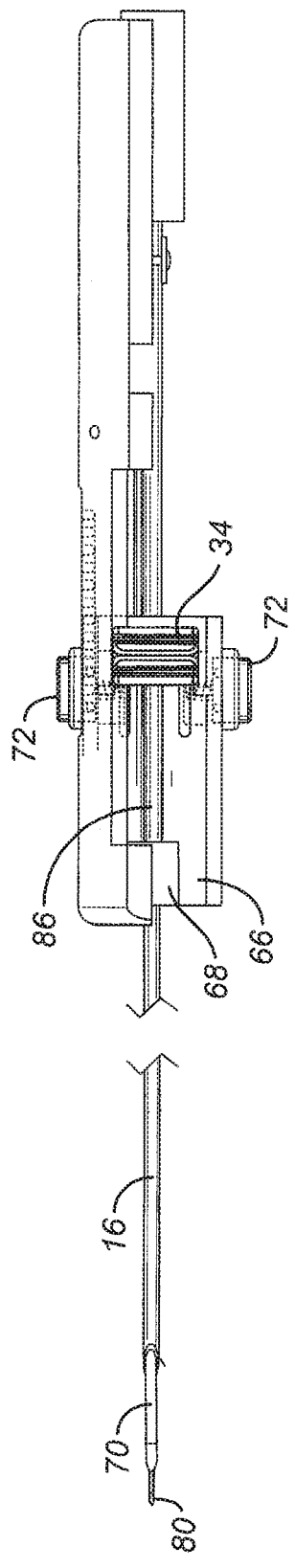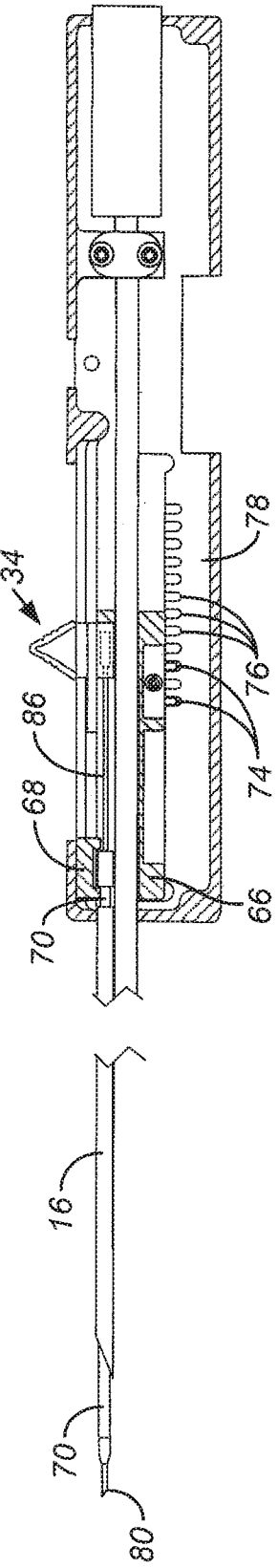

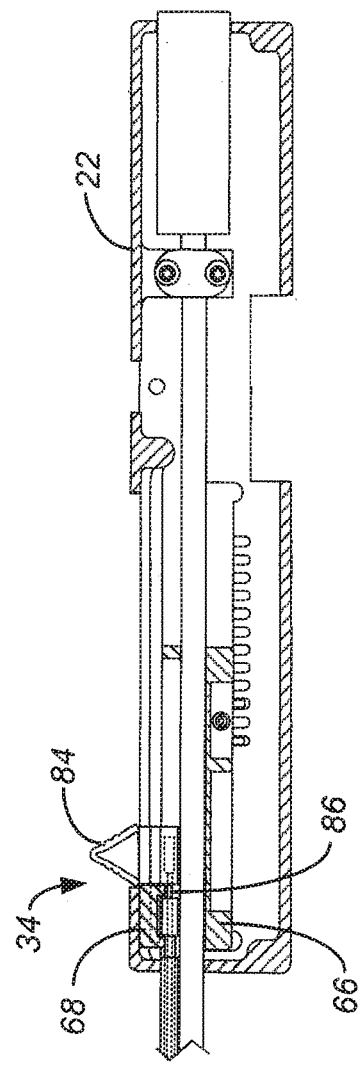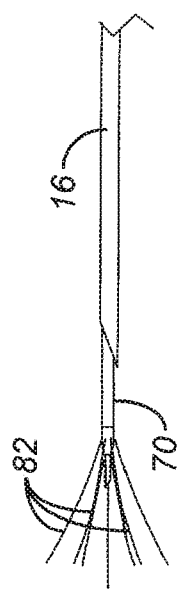
*FIG. 9*
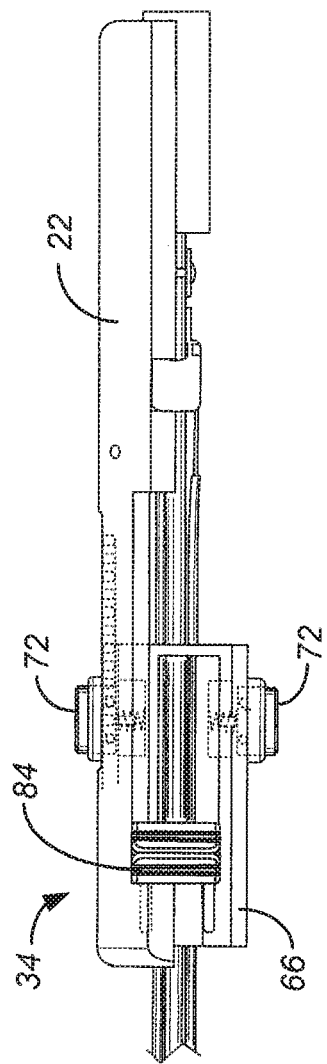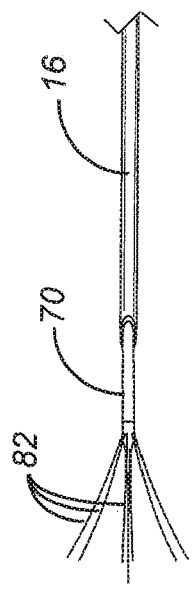
*FIG. 10*

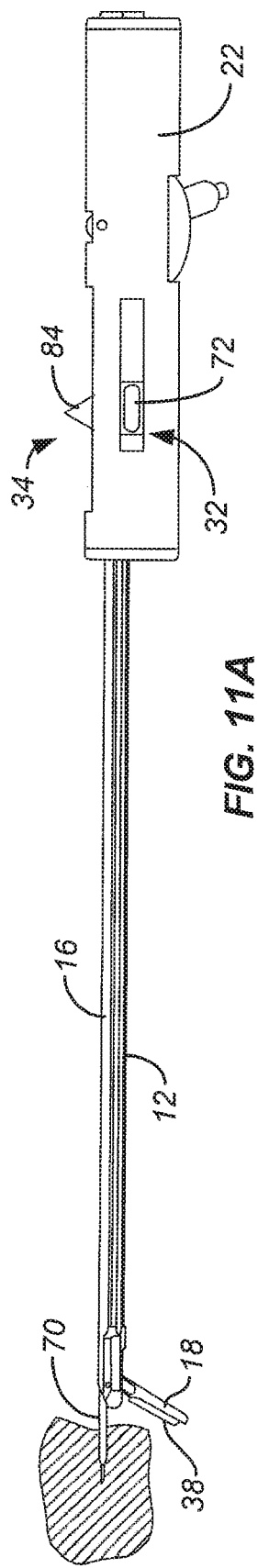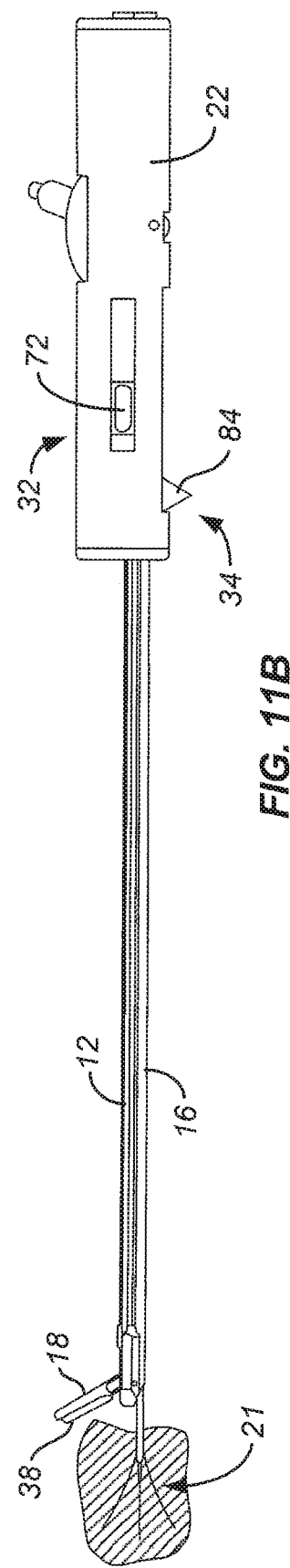

ABLATION DEVICE WITH ARTICULATED IMAGING TRANSDUCER

CROSS-REFERENCE TO RELATED APPLICATIONS

This application is a continuation of U.S. patent application Ser. No. 14/989,732, filed Jan. 6, 2016, now U.S. Pat. No. 10,610,197; which is a continuation of U.S. patent application Ser. No. 13/484,076, filed May 30, 2012, now U.S. Pat. No. 10,595,819; which is a continuation-in-part of U.S. patent application Ser. No. 13/023,383, filed Feb. 8, 2011, now U.S. Pat. No. 8,206,300; which is a continuation of PCT Application No. PCT/US09/54956, filed Aug. 25, 2009; which is a continuation-in-part of U.S. patent application Ser. No. 12/198,861, filed on Aug. 26, 2008; U.S. patent application Ser. No. 13/484,076 is also a continuation-in-part of U.S. patent application Ser. No. 12/973,587, filed Dec. 20, 2010, now U.S. Pat. No. 8,506,485; which is a continuation of U.S. patent application Ser. No. 11/564,164, filed Nov. 28, 2006, now U.S. Pat. No. 7,874,986; which is a continuation-in-part of application Ser. No. 11/409,496, filed Apr. 20, 2006, now U.S. Pat. No. 7,815,571; the full disclosures of which are incorporated herein by reference.

BACKGROUND OF THE INVENTION

1. Field of the Invention

The present invention relates generally to medical devices and methods. More particularly, the present invention relates to an imaging and therapy device having a deployable treatment needle or needles and a pivotal imaging array.

Uterine fibroids are benign tumors in the uterine wall and are the most common tumor of the female pelvis. Fibroids afflict up to 30% of women of childbearing age and can cause significant symptoms including discomfort, pelvic pain, mennorhagia (excessive bleeding), anemia, infertility, and miscarriage. While fibroids may be located in the muscle (intramural), adjacent to the endometrium (submucosal), or in the outer layer of the uterus (subserosal), and can grow up to several centimeters in diameter.

Current treatments for fibroids include both pharmaceutical and surgical intervention. Pharmaceutical treatments include the administration of NSAIDS, estrogen-progesterone combinations, and the like. Medications, however, are generally ineffective and are palliative rather than curative. Surgical interventions include myomectomy, where fibroids are removed in an open surgical procedure requiring laparotomy and general anesthesia, and hysterectomy, involving complete surgical removal of the uterus. Both these procedures are long and have significant blood loss.

As improvements over open surgical procedures, several minimally invasive procedures have been developed. Laparoscopic myomectomy is a laparoscopic procedure requiring highly skilled laparoscopic gynecologists. Uterine artery embolization relies on blocking the uterine artery supplying blood to the fibroid by injecting small particles. While sometimes effective, common complications of arterial embolization include infection, premature menopause, and severe pelvic pain. A third approach relies on complete endometrial ablation, which is generally effective for treating bleeding but less reliable for treating fibroids.

More recently, and of particular interest to the present invention, the use of radiofrequency needles and other ablation elements for treating individual fibroids via a transvaginal approach has been proposed. As described, for example, in U.S. Patent Publications 2006/0189972; 2007/0179380; and 2008/0033493, each of which is commonly assigned with the present application, a probe carrying a curved needle is used to treat individual fibroids. The probe carries on-board ultrasonic or other imaging so that the needle can be guided into the fibroid under direct observation. While highly effective in many cases, accurate advancement of a curved needle into a fibroid can be problematic. Moreover, use of a single needle does not always deliver sufficient energy to fully ablate relatively large fibroids.

For these reasons, it would be desirable to provide alternative devices and methods for treating, ablating, or removing uterine fibroids and other tissue masses. It would be particularly desirable if such methods and devices were able to treat uterine fibroids which are large, difficult to penetrate, or which otherwise resist treatment with curved and laterally deployed needles. At least some of these objectives will be met by the inventions described below.

2. Brief Description of the Background Art

The following US Patent Publications discussed above are relevant to the present invention: 2006/0189972; 2007/0179380; and 2008/0033493. See also US Patent Publication 2007/0249936. The disclosures of each of these applications is incorporated herein by reference.

BRIEF SUMMARY OF THE INVENTION

The present invention provides apparatus and methods for imaging and treating fibroids and other tumors and tissue masses located in the walls of a uterus or other body cavity. The apparatus and systems comprise a straight shaft having a distal end and a proximal end. A delivery needle, preferably straight, is reciprocatably coupled to the shaft, typically being mounted in a straight lumen in the shaft, so that a tissue-penetrating tip of the needle can be distally advanced from the shaft along an axial path. The delivery needle may carry tines forming a needle array, deployable from within the delivery needle. A tip or other structure is pivotally attached to the distal end of the shaft and is moveable between a position parallel to the axial path and a position at an acute or right angle relative to the axial path. The pivotable tip carries or comprises an ultrasonic imaging array, and the tip can be oriented to align a field of view of the imaging array with the needle as the needle is advanced along the axial path.

The combination of a straight shaft, delivery needle, and pivotally attached tip or imaging array has a number of advantages. The straight shaft and needle can be advanced with precision into tissue surrounding the body cavity, where the needle can be made sufficiently strong to resist unwanted deflection of the type which could occur with other needle configurations. The use of a delivery needle and shaft also enables and facilitates the deployment of a needle array, including a plurality of tines, from the delivery needle to increase the volume of tissue being treated with the needle array. The pivotable imaging array allows straightening of the imaging array to provide a low profile for introduction through the cervix into the uterus, while also allowing reorientation to cover a wide range of viewing fields after entering the uterus or other body cavity to permit locating fibroids and other tumors and to further follow the advance of the needle array into the fibroids or other tumors. It should be noted that in the preferred embodiment, the delivery needle is for delivery only, and does not provide treatment. In alternative embodiments, the delivery needle may be used for treatment. The pivotable tip further allows the effective field of view of the ultrasound image to be increased by pivoting the tip, which has the effect of sweeping the ultrasound image. The tip may be pivoted to enhance the view of the delivery needle and/or the needle array, including tines.

In a preferred embodiment, an imaging and therapeutic delivery system includes a straight shaft having a distal end and a proximal end and a straight needle reciprocatably coupled to the shaft so that a tissue-penetrating tip on the needle can be distally advanced from the shaft along an axial path and a tip pivotally attached to the distal end of the shaft and movable between a position parallel to the axial path and a position at an acute or right angle relative to the axial path. An ultrasonic imaging array is carried by the pivotally attached tip, wherein the tip can be oriented to align a field of view of the imaging array with the needle as it is advanced along the axial path so as to sweep the ultrasound field of view relative to the needle and anatomy to be imaged. The tip is offset from the axial path of the needle.

In certain preferred embodiments, an imaging and therapeutic delivery system includes a straight shaft having a distal end and a proximal end. A needle is reciprocatably coupled to the shaft so that a tissue-penetrating tip on the needle can be distally advanced from the shaft along an axial path, said needle exiting said shaft at an angle of 0 degrees relative to said shaft. A tip is pivotally attached to the distal end of the shaft and movable between a position parallel to the axial path and a position at an acute or right angle relative to the axial path. An ultrasonic imaging array is carried by the pivotally attached tip, wherein the tip can be oriented to align a field of view of the imaging array with the needle as the needle is advanced along the axial path so as to sweep the ultrasound field of view relative to the needle and anatomy to be imaged.

In the preferred embodiment, the imaging array will be formed on an imaging core, where the imaging core is removably positionable in the straight shaft so that the imaging array extends into the pivotally attached tip. The straight shaft will usually be rigid while the imaging core is relatively flexible, allowing the imaging core to bend at the point where the tip is pivotally attached to the shaft. In alternate embodiments, the needle assembly may be attached directly to the ultrasound probe or the imaging core may be hinged at the point where the tip is pivotally attached to the shaft.

In certain preferred embodiments, the delivery needle will carry a needle array having at least one tine which can be advanced from the delivery needle, usually carrying a plurality of tines, where the tines are reciprocatably attached to the delivery needle to permit deployment and retraction, usually after the delivery needle has been advanced into target tissue. A plurality of tines will usually be arranged to radially diverge from the delivery needle as the tines are distally advanced. Optionally, at least one additional tine may be reciprocatably mounted on the delivery needle in a range to be advanced axially from the needle, often forming a center axis to a symmetric deployment of radially diverging tines. In order to localize the treatment, the tines may be electrically conductive while the delivery needle itself is electrically non-conductive or insulating. In such cases, the tines may be arranged to be connected to a single pole of an electrosurgical power supply in order to provide for monopolar treatment. Alternatively, a certain number of the tines may be adopted to one pole of the power supply while others are connected to the other pole, providing for bipolar treatment.

In certain exemplary embodiments, the imaging and therapeutic delivery system will further comprise a handle attached to the proximal end of the straight shaft. The handle may include a lever coupled to the pivotally attached distal tip by one or more pull rods. The lever can be pulled or pushed to actuate the pull rod(s) to pivot the tip. Additionally, the handle may include a first slide mechanism coupled to the delivery needle, where the slide mechanism can be reciprocated to advance and retract the needle along the axial path. In the embodiments which include the plurality of tines, the tines may be reciprocatably attached to the delivery needle and connected to a second slide mechanism on the handle, optionally being disposed on the first slide mechanism itself, to advance and retract the tines relative to the needle. Optionally, a stop structure may be disposed on the pivotally attached tip so that the stop structure prevents advancement of the needle when the tip is parallel to the axial path of the needle.

The present invention also comprises methods for treating uterine fibroids. The methods include introducing a straight shaft into the uterus. Uterine fibroids are then located using an ultrasonic imaging transducer carried by or formed as part of a pivotable tip attached to a distal end of the shaft. The tip is pivoted to reposition a field of view of the ultrasonic transducer carried by the tip. Optionally, the tip may block advancement of the needle when disposed parallel to the shaft (prior to deployment) and allow advancement when pivoted from the parallel orientation. A delivery needle may be axially advanced from the distal tip of the shaft into tissue near or in a uterine fibroid located using the ultrasonic transducer. Advancement of the needle may be observed by the transducer by aligning the field of view with the needle advancement.

In preferred aspects of the methods of the present invention, the shaft is introduced to the uterus via a transvaginal and transcervical introduction. Locating fibroids may comprise manually rotating and translating the shaft to scan the uterine wall with the ultrasonic transducer. Locating may also comprise pivoting the ultrasonic transducer to adjust the field of view. Optionally, an array including a plurality of tines may be advanced from the delivery needle after the needle has been advanced into tissue at or near the uterine fibroid. This method will sweep the ultrasound field of view relative to the needle and anatomy to be imaged. The fibroid is then treated by delivering energy from the needle and/or tines into the fibroid, typically radiofrequency energy, including both monopolar and bipolar radiofrequency energy. Usually, the tines will be electrically active to deliver the radiofrequency energy while the delivery needle is electrically non-conductive to limit the distribution of energy in the uterine wall or other tissue being treated.

BRIEF DESCRIPTION OF THE DRAWINGS

FIGS. 1A and 1B are perspective views of an imaging and therapeutic delivery system constructed in accordance with the principles of the present invention shown with portions broken away. In FIG. 1A, a delivery needle and array including radially diverging tines are retracted within the shaft of the device, and a pivotally attached tip is shown in axial alignment with the axial deployment path of the needle. In FIG. 1B, the delivery needle and associated tines are shown in their deployed configuration with the pivotally attached tip shown oriented at an acute angle relative to the axial advancement path of the needle.

FIGS. 5 and 6 are side and top views of the imaging and therapeutic delivery system shown with portions broken away in a non-deployed configuration.

FIGS. 7 and 8 are views similar to FIGS. 5 and 6, except that the delivery needle has been deployed and the pivotally attached tip has been positioned at an acute angle.

FIGS. 9 and 10 are views similar to FIGS. 5 and 6 and FIGS. 7 and 8, respectively, further illustrating the deployment of the needle array, comprising radially diverging tines from the delivery needle.

FIGS. 11A and 11B illustrate deployment of the delivery needle and tines into tissue.

DETAILED DESCRIPTION OF THE INVENTION

Figure 1B:
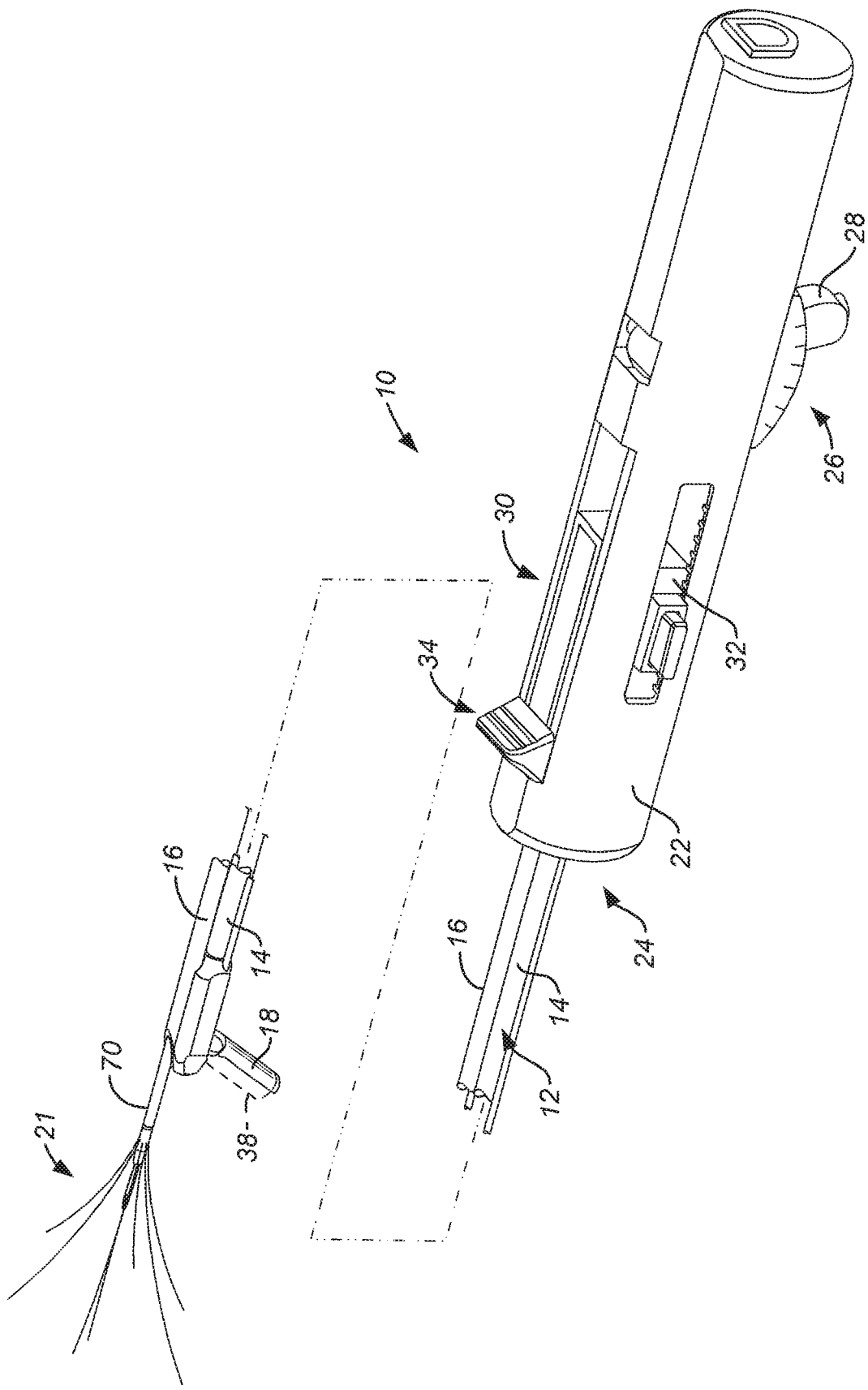

Referring to FIGS. 1A and 1B, an imaging and therapeutic delivery system constructed in accordance with the principles of the present invention comprises a straight shaft assembly 12 including a hollow rod 14 and a needle tube 16. A tip 18 which is adapted to receive an ultrasonic imaging array (shown in broken line at 38) is pivotally attached to a distal end 20 of the hollow rod 14 of the straight shaft assembly 12. A needle and tine array 21 (FIG. 1B) is deployed through a lumen or central passage in the needle tube 16 at a distal end 20 of the shaft assembly 12. A handle assembly 22 is attached to a proximal end 24 of the straight shaft assembly 12 and includes a pivoting mechanism 26, typically found on its lower surface as illustrated, for selectively pivoting the imaging array tip 18 between a low profile configuration where the tip 18 is axially aligned with the axis of the shaft assembly 12, as illustrated in FIG. 1A, and a deflected configuration where the tip 18 is oriented at an acute or right angle relative to the axis of the shaft, as illustrated in FIG. 1B. The tip 18 may be placed in its axially aligned, low profile configuration for introduction to the body cavity, for example through the cervix into the uterus, and may be shifted to its deflected configuration in order to image tissue and/or to track deployment of the needle/tine array 21. As described in more detail below, the pivoting mechanism 26 includes a lever 28 which may be manually retracted from the distally advanced configuration shown in FIG. 1A to the proximally retracted configuration shown in FIG. 1B in order to pivot the tip 18.

The handle 22 will also include a delivery needle/tine deployment mechanism 30 which includes a first slide subassembly 32 and a second slide subassembly 34. The handle will usually further include a port 36 at its proximal end. Port 36 allows introduction of an ultrasonic or other imaging core, where the imaging core has an imaging array 38, typically an ultrasonic imaging array as described in detail in copending application Ser. No. 11/620,594; and parent application Ser. Nos. 11/564,164; and 12/973,587, the full disclosures of which are incorporated herein by reference. The proximal end of the handle will also allow electrical connections to be made to the needle/tine array. Additionally, the distal end of the handle will provide a standard luer connection for the infusion of non-conductive coupling fluids.

Figure 2:
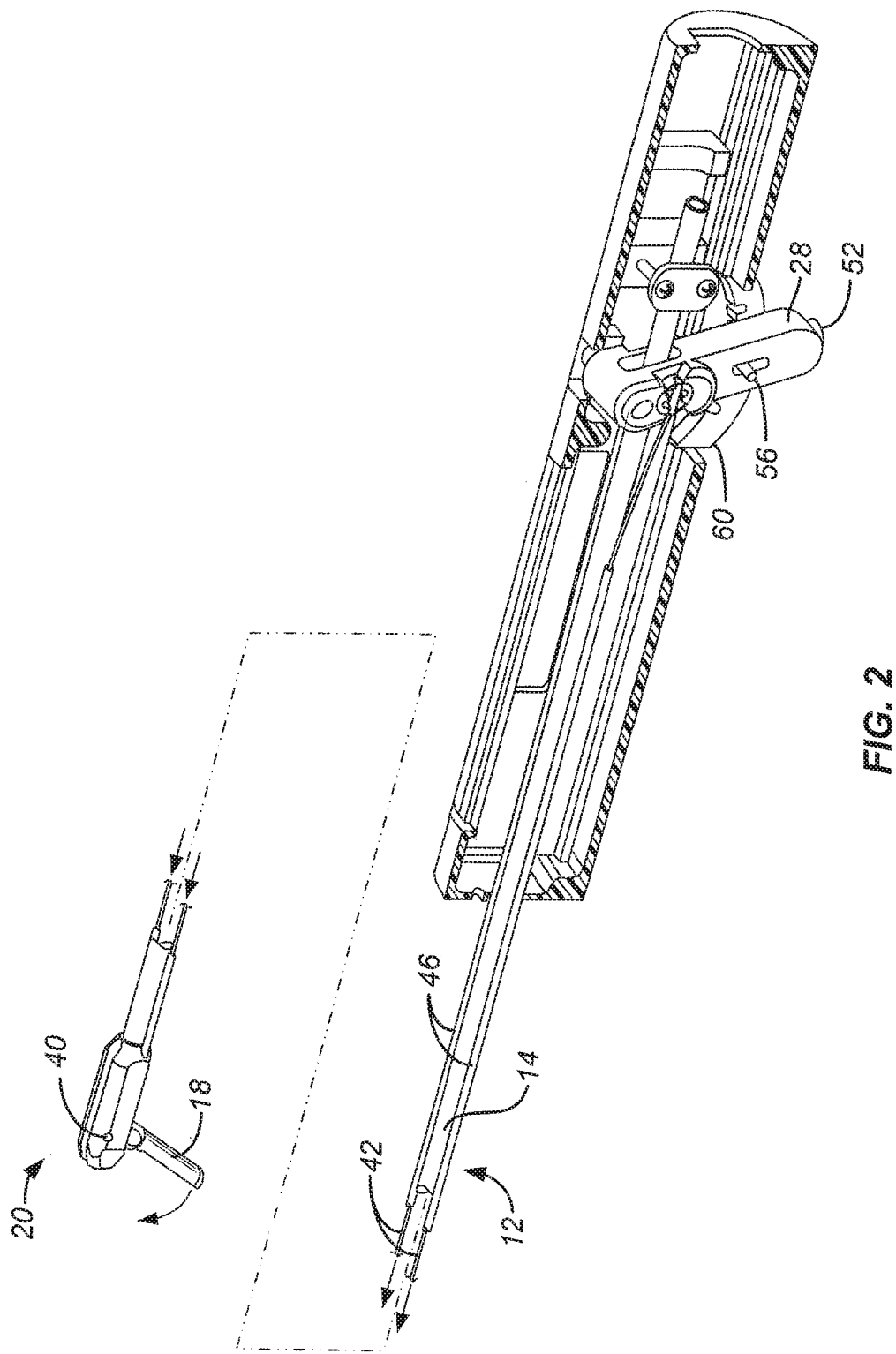
FIG. 2 illustrates the imaging and therapeutic delivery system of FIGS. 1A and 1B in cross-section.
Figure 2A:
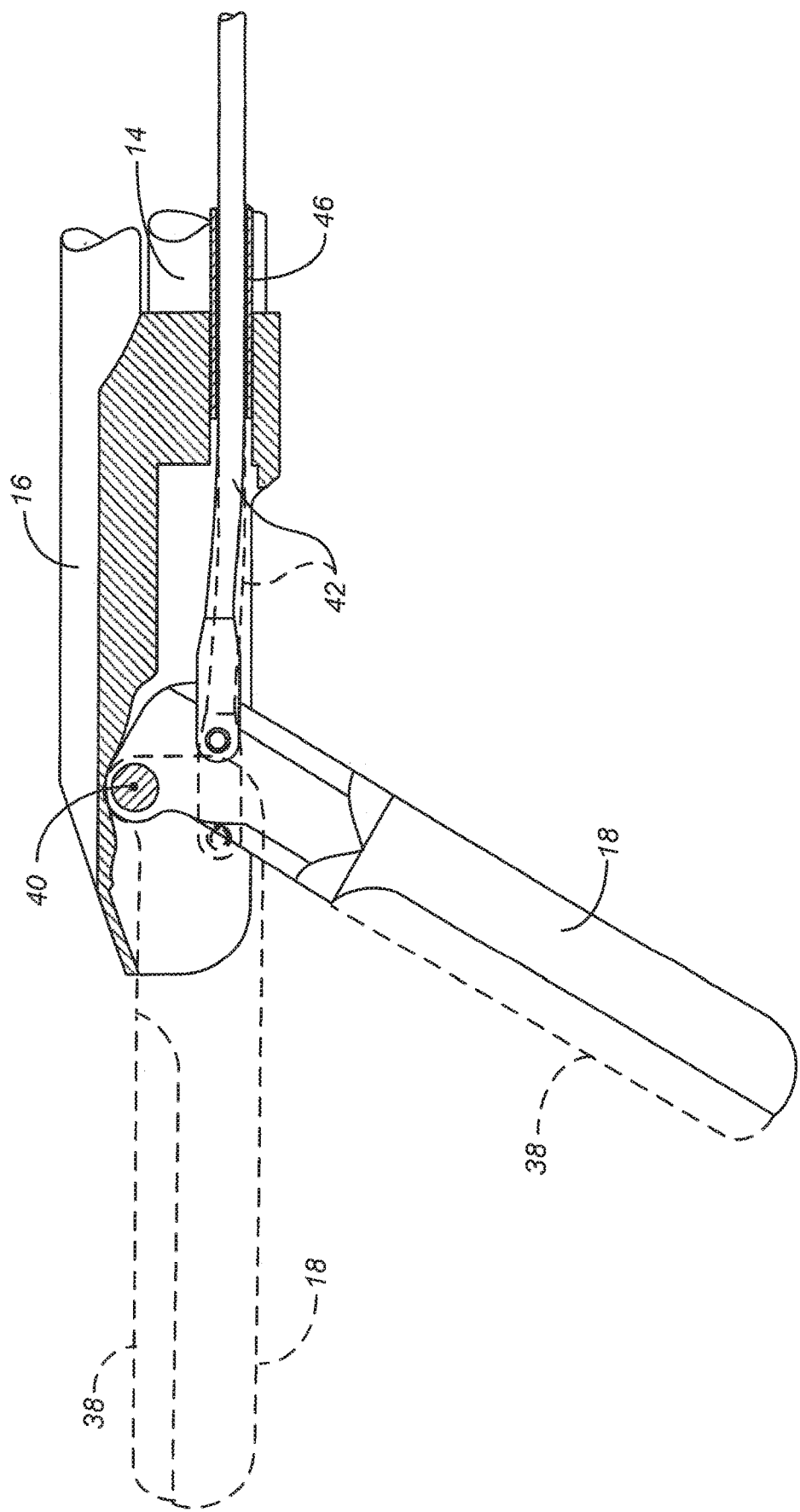
FIG. 2A is a detail of the distal tip of the device illustrated in FIG. 2.
Figure 2B:
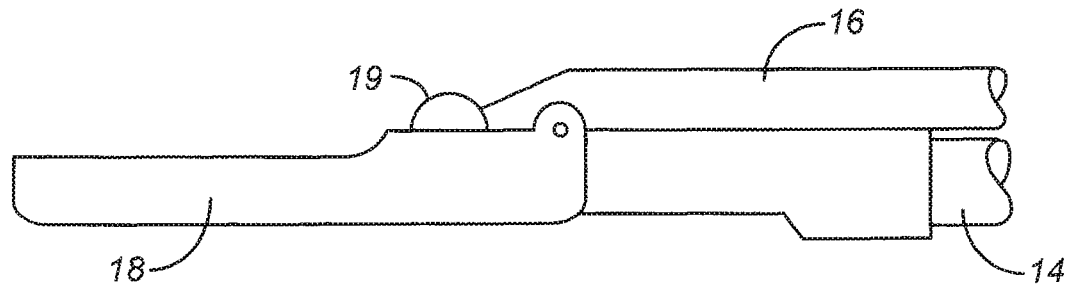
FIGS. 2B and 2C illustrate a stop structure on the pivotally attached tip which prevents needle advancement prior to deployment of the tip.
Figure 2C:
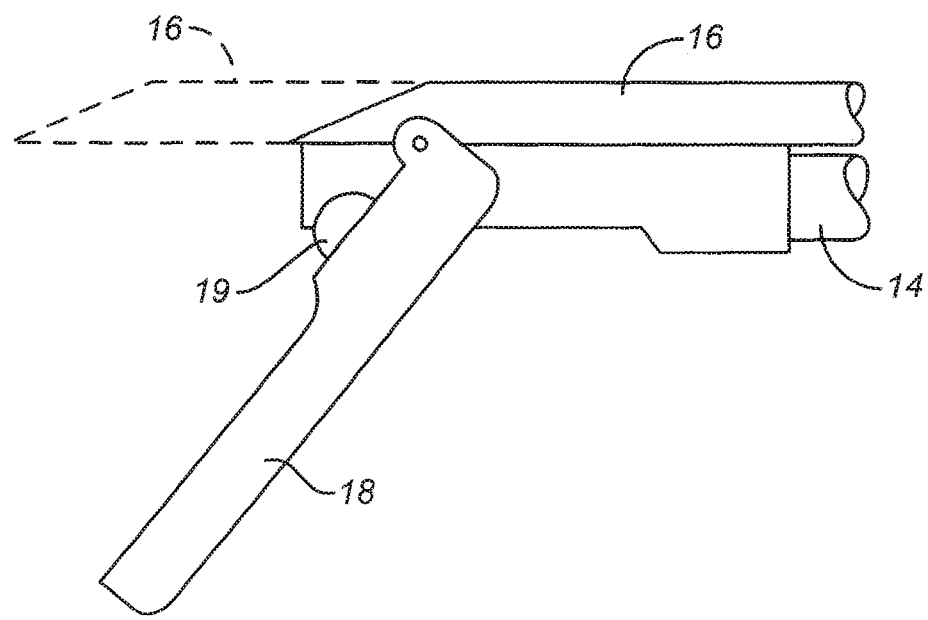

Optionally, a stop structure 19 may be attached to an upper surface of the pivotally attached tip 18, as illustrated in FIGS. 2B and 2C. When the tip 18 is parallel to the axis of the shaft (hollow rod 14), the stop structure 19 will block the advancement path of the needle 16 (as shown in FIG. 2B). This is advantageous since it prevents accidental needle advancement while the shaft assembly 12 is in the introductory configuration. Deployment of the tip 18, as shown in FIG. 2C, moves the stop structure 19 out of the advancement path of the needle 16, as described below.

Figure 3A:
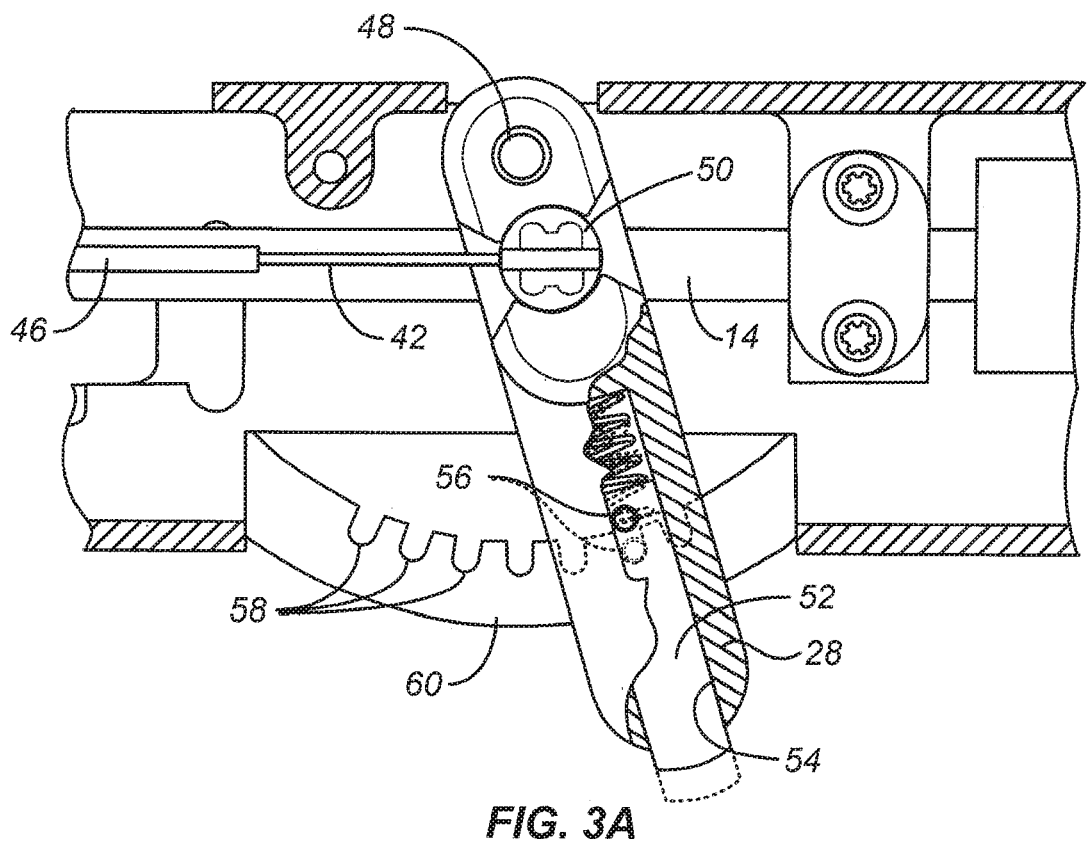
FIGS. 3A and 3B illustrate the pivotal tip deployment mechanism in detail, also in cross-section.
Figure 3B:
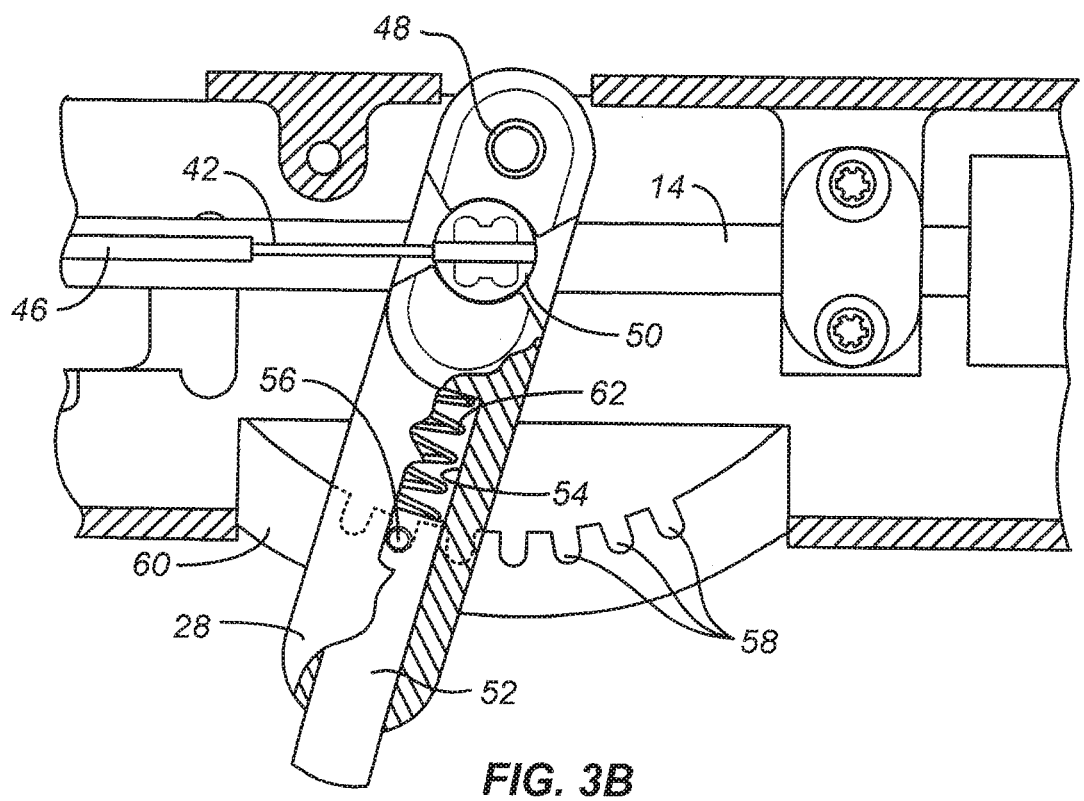

Referring now to FIGS. 2, 2A, 3A, and 3B, operation of the pivot mechanism 26 for selectively deflecting the tip 18 disposed at the distal end of the straight shaft assembly 12 will be described. For clarity, components of the first slide assembly 32 and second slide assembly 34 have been removed from the view in FIG. 2. The tip 18 is pivotally attached at the distal end 20 of the straight shaft assembly 12 by a pivot pin 40 or similar structure, as best seen in FIG. 2A. A pair of pull rods 42 are attached at anchors 44 so that drawing the wires in a proximal direction will deflect the tip 18 from an axially aligned configuration, as shown in broken line in FIG. 2A, to the deflected configuration, as shown in full line in FIG. 2A. The rods 42 extend through tubes 46 disposed on each side of the hollow rod 14 of the shaft assembly 12. As best seen in FIGS. 3A and 3B, the rods 42 are attached at their proximal ends to a rotating anchor 50 disposed in lever 28. Thus, by drawing the lever 28 proximally, as shown in FIG. 3A, the tip 18 may be laterally deflected, as shown in full line in FIG. 2A. Conversely, by pushing the lever 28 in a distal direction, as shown in FIG. 3B, the tip 18 may be returned to the axially aligned configuration as shown in broken line in FIG. 2A. The lever 28 is pivotally attached to the body of handle 22 by a pivot pin 48 so that the anchor 50 is offset from the point of rotation of the lever 28. Thus, the anchor 50 is actually translated as the lever is rotated back and forth about the pivot pin 48.

A locking pin 52 allows the lever 28 to be selectively locked in place to hold the pivot tip 18 in a fixed orientation. Locking pin 52 is mounted in a central passage 54 of the lever 28 and carries a pin 56 which seats in one of a plurality of pockets 58 formed in an arcuate locking strip 60. Thus, the lever 28 can be released by pressing the pin 52 against spring 62 so that the pin 56 is lifted out of the pocket 58, as shown in FIG. 3A. In this configuration, the lever may be moved freely back and forth to deploy the tip 18. When the tip 18 is in its desired location, the locking pin 52 may be released to permit pin 56 to engage the closest pocket 58 where it is held in place by spring 62. It will be appreciated that the lever 28 will typically be advanced forwardly to close the tip 18 to a low profile configuration for introducing the imaging and therapy delivery system 10 to the patient for treatment, for example through the cervix into the uterus. Once in place, the lever 28 can be unlocked using the locking pin 52 and oriented to a desired angle relative to the shaft assembly 12 to permit imaging and, in particular, to allow advancement of the delivery needle 70 in the tissue to be observed.

Figure 4A:
FIGS. 4A-4C illustrate the relative movement of the deployment mechanism and the pivotal tip, as the deployment mechanism is actuated.
Figure 4B:
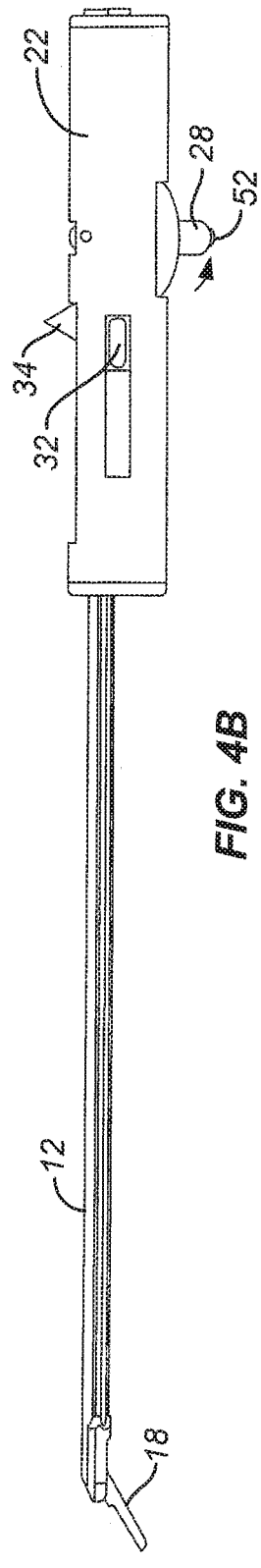
Figure 4C:
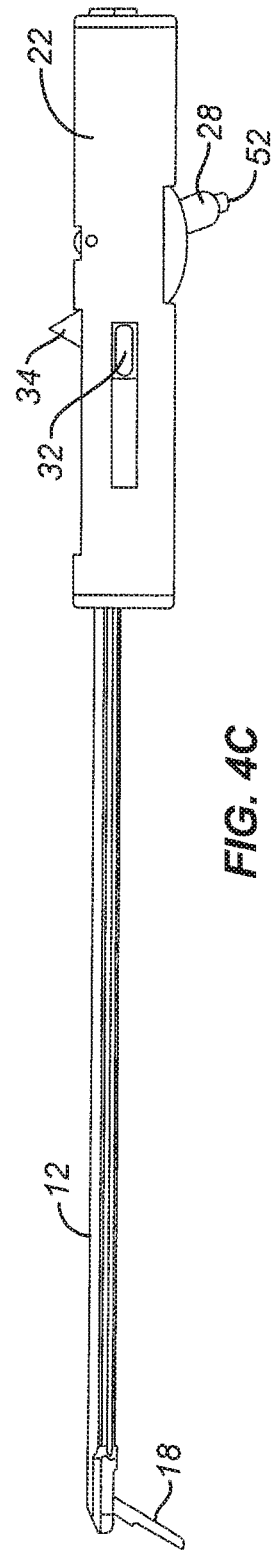

Referring now to FIGS. 4A-4C, use of the lever 28 for deflecting the tip 18 is illustrated. Initially, the tip 18 is axially aligned with the axis of the shaft assembly 12 and the lever 28 is in its forward or distal-most position, as shown in FIG. 4A. By depressing locking pin 52, as shown in FIG. 4B, lever 28 may be drawn proximally as indicated by the adjacent arrow, to deflect the tip 18 away from the axis of shaft 12, as shown by the arrow adjacent the tip in FIG. 4B. When the lever 28 reaches its fully proximal position, as shown in FIG. 4C, the tip 18 has been fully deflected away from the axis of shaft assembly 12. Note that slide subassemblies 32 and 34 (for extending delivery needle 70 and needle array 21) have not been activated in FIGS. 4A-4B.

Referring now to FIGS. 5-10, operation of the first slide subassembly 32 and the second slide subassembly 34 will be described. For clarity, portions of the pivot mechanism 26 have been removed from these views. Prior to deployment, as shown in FIGS. 5 and 6, the needle/tine array 21 is fully drawn into the central passage of needle tube 16. Needle tube 16 has an open distal tip 64 through which the delivery needle and tines will emerge when advanced using the slide subassemblies 32 and 34.

The first slide subassembly 32 comprises a reciprocating carriage 66 having a coupling 68 attached to a proximal end of the needle 70. The carriage 66 may be axially advanced and retracted by manually pressing buttons 72 to disengage pins 74 (FIG. 5) from pockets 76 in a straight locking strip 78. Once the pins 74 are disengaged, the carriage 66 may be distally advanced, as shown in FIGS. 7 and 8, to advance tip 80 of needle 70 from the distal end of the needle tube 16. The buttons 72 may then be released to allow pins 74 to reenter the adjacent pockets 76 in the locking strip 78, thus locking the needle 70 in place.

Referring now in particular to FIGS. 9 and 10, a plurality of radially diverging tines 82 may be deployed from the distal end of needle 70 using the second slide subassembly 34 which includes a thumb slide 84. The thumb slide 84 is reciprocatably carried in the carriage 66 so that the thumb slide will advance the tines relative to the needle. The thumb slide is connected to a tine rod 86 which enters a hollow central passage or lumen of the needle 70 and is coupled to the plurality of tines 82 so that advancement of the thumb slide 84 from the retracted position shown in FIGS. 7 and 8 to the distally advanced position shown in FIGS. 9 and 10 causes the tines 82 to emerge from the distal end of the needle 70. The tines 82 are preferably formed from a straight, resilient metal, such as stainless steel, nickel titanium, or the like, and are deflected outwardly by ramps (not shown) in the distal end of the needle. Optionally, a lockout circuit (not shown) may be provided to prevent energizing the tines if the tines are not fully advanced.

The use of the imaging and therapeutic delivery system 10 of the present invention is illustrated in FIGS. 11A and 11B. After imaging using the imaging array 38 carried on or in tip 18, the needle 70 is advanced into target tissue identified by the imaging using the first slide subassembly 32, as shown in FIG. 11A. Usually, the position of the tip 18 will be adjusted to assure that travel of the needle 70 into the tissue may be observed. After the location of the needle tip 80 has been confirmed, the thumb slide 84 of the second slide subassembly 34 may then be advanced, as shown in FIG. 11B, to extend the tines 82 into the tissue. In the preferred embodiments of the present invention, the needle 70 and tines 82 will be rotatably connected to the remainder of the device to allow the handle to be rotated, thus rotating the imaging array 38, to facilitate imaging even after the needle and tines have been deployed.

Figure 12:
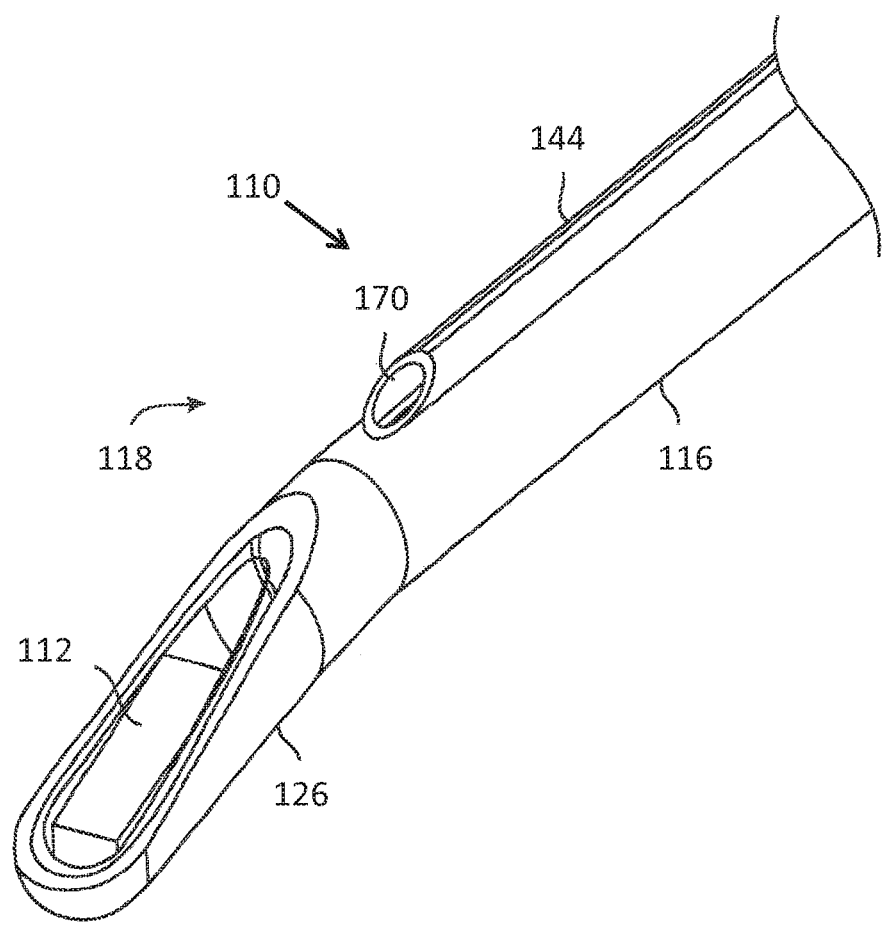
FIG. 12 illustrates a system without an ablation needle.

Referring now to FIG. 12, a delivery system 110 without an ablation needle is illustrated. A deflectable distal tip 126 of the rigid shaft 116 may be deflected by the use of pull or tensioning wire(s) housed within the shaft 116. Deflection may occur at a true mechanical pivot or at a flexible zone at the shaft distal end 118. As discussed above, when the delivery shaft 116 is deflectable by a user, various needles may be used to match the amount of deflection provided by the distal tip 126 as well as the amount of tilt provided by the ultrasound array 112. Hence, a needle guide 144 will typically be empty until the distal end 118 of the shaft 116 is deflected. For example, the shaft 116 may be inserted in a straight configuration. The distal tip 126 may then be deflected until a target anatomy is identified. A needle is then back loaded within the guide passage 170 that corresponds to the amount of the deflection.

Table I below illustrates possible viewing angles κ that may be achieved by the cumulative effects of the shaft bending angle β (e.g., either through active deflection of the distal tip or a pre-shaped or pre-bent distal tip) and the ultrasound tilting angle α. The matching needle angles θ based on the possible viewing angles κ are further illustrated. In example 1, the shaft 116 is in a straight configuration so that the viewing angle κ is provided solely by the tilting angle α of the ultrasound array 112. In example 4, the needle 114 will have a straight configuration. In example 5, a non-tilted and non-bent ultrasound array 112 version is covered. It will be appreciated that the viewing angle κ will be more than the bend angle θ of the shaft 116 due to the additive effect of the tilting angle α of the ultrasound array 112. This allows the bend on the distal tip 126 of the shaft 116 to be shallower without compromising the cumulative viewing angle κ, which is of particular benefit for patient insertion considerations. In the case of a deflectable distal tip 126 in which insertion may be implemented in a straight configuration, the tiled ultrasound angle α still aids in reducing the needle angle θ.

TABLE I

| Example | Viewing Angle (κ) | Tilt Angle (α) | Bend Angle (β) | Needle Angle (θ) |
|---------|-------------------|----------------|----------------|------------------|
| 1 | 7°-10° | 7°-10° | 0° | 80° |
| 2 | 20° | 7°-10° | 10°-13° | 70° |
| 3 | 45° | 7°-10° | 35°-38° | 45° |
| 4 | 90° | 7°-10° | 80°-83° | 0° |
| 5 | 0° | 0° | 0° | 90° |

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of treating a uterine fibroid, the method comprising:
   transcervically introducing into a uterus a rigid shaft comprising a stop structure and a tip attached to a distal end of the shaft, the tip including an ultrasound transducer;
   deflecting the tip to reposition a field of view of the ultrasound transducer;
   locating the uterine fibroid using the ultrasound transducer;
   moving the stop structure out of an advancement path of a needle advanceable from a needle guide delivered transcervically into the uterus;
   transcervically advancing the needle from the transcervically delivered needle guide and into the uterine fibroid after the stop structure is moved out of the advancement path, wherein the needle is advanced by adjusting a deployment mechanism coupled to the needle guide and separate from the stop structure;

advancing a plurality of tines from the transcervically advanced needle and into the uterine fibroid after the stop structure is moved and the needle is advanced into the uterine fibroid, wherein the plurality of tines is advanced by further adjusting the deployment mechanism; and observing the needle, the plurality of tines, and the uterine fibroid using the ultrasound transducer.

2. The method of claim 1, wherein locating the uterine fibroid comprises manually rotating and/or torquing the rigid shaft to scan the uterus with the ultrasound transducer.

3. The method of claim 1, further comprising delivering radiofrequency energy to the uterine fibroid through the plurality of tines.

* * * * *